United States Patent [19]

Okorodudu

[11] 3,980,574

[45] Sept. 14, 1976

[54] LUBRICANT CONTAINING DIORGANOPHOSPHORUS DERIVATIVES OF URETHANE AS ANTIWEAR AGENTS

[75] Inventor: Abraham O. M. Okorodudu, West Deptford, N.J.

[73] Assignee: Mobil Oil Corporation, New York, N.Y.

[22] Filed: June 12, 1975

[21] Appl. No.: 586,462

[52] U.S. Cl. .............................................. 252/49.9
[51] Int. Cl.$^2$ ................. C10M 1/10; C10M 3/02; C10M 5/02; C10M 7/02
[58] Field of Search ............................... 252/49.9

[56] References Cited
UNITED STATES PATENTS

| | | | |
|---|---|---|---|
| 3,677,943 | 7/1972 | Nnadi | 252/49.9 |
| 3,775,323 | 11/1973 | Dubourg | 252/49.9 |
| 3,803,038 | 4/1974 | Olszewski | 252/49.9 |

*Primary Examiner*—Delbert E. Gantz
*Assistant Examiner*—I. Vaughn
*Attorney, Agent, or Firm*—Charles A. Huggett; Raymond W. Barclay; Claude E. Setliff

[57] ABSTRACT

The load carrying ability of a lubricant is improved by adding to such lubricant an effective amount of diorganophosphorus derivative of urethane (ethyl carbamate).

8 Claims, No Drawings

LUBRICANT CONTAINING DIORGANOPHOSPHORUS DERIVATIVES OF URETHANE AS ANTIWEAR AGENTS

BACKGROUND OF THE INVENTION

1. Field of the Invention

The invention is concerned with improving the load carrying ability of a lubricant and with compositions containing same. In particular, the additive is a diorganophosphorus derivative of urethane.

2. Discussion of the Prior Art

It is known that sliding or rubbing metal or other solid surfaces are subject to wear under conditions of extreme pressure. Wearing is especially acute in modern engines in which high temperatures and contact pressures are present. Under such conditions, severe erosion of metal surfaces can take place even with the newer lubricants, in the absence of load carrying additives.

Certain phosphorus compounds are known for use as load bearing additives. For example, U.S. Pat. No. 3,591,501 discloses the use of a hydroxy-organophosphine oxide. U.S. Pat. No. 3,583,915 teaches the use of a di(organo)hydrogen phosphonate to impart load carrying properties to a lubricant. No patent, or other reference, is known, however, that teaches or suggests the compounds disclosed herein as load carrying additives.

SUMMARY OF THE INVENTION

In accordance with the invention, there is provided a lubricant composition comprising a major proportion of a lubricant and a minor amount sufficient to impart load-carrying properties thereto of a diorganophosphorus compound of the formula:

wherein R is a $C_1$–$C_{25}$ hydrocarbyl and $m$ is zero or one. "Hydrocarbyl" will include, but will not be specifically limited to methyl, ethyl, butyl, octyl, dodecyl, octadecyl, eicosyl, pentacosyl, phenyl, naphthyl, anthryl, cyclopropyl, cyclopentyl, cyclohexyl, methyl-, ethyl-, butyl-, octylphenyl, nonylphenyl, benzyl and phenethyl.

DESCRIPTION OF SPECIFIC EMBODIMENTS

The additives useful in the practice of this invention may be prepared in accordance with the following reaction:

Alternative methods that may be employed are:

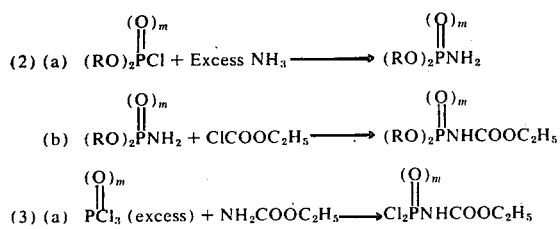

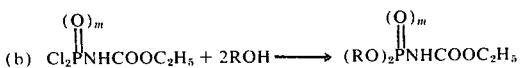

These compounds may be prepared in one of several ways, as shown by the above equations. One general procedure [(1) above] involves the dropwise addition of a diorgano halophosphate or diorgano halophosphite to a stirred solution of an excess of ethyl carbamate in a suitable solvent such as 1,2-dimethoxyethane, while heating the reaction mixture slowly to reflux. After the addition, the mixture is refluxed for 3–4 hours, cooled and treated with water and benzene. The organic portion is further washed with water, dried and stripped of solvent to give the product.

Another method for preparing the compounds [(2) above] involves the addition of an excess amount of ammonia to a cold (5°–10°C) solution of a diorgano halophosphate or halophosphite in a solvent, and the resulting mixture is filtered to remove ammonium chloride precipitate. At room temperature, the filtrate is added to a stirred solution of an equimolar amount of ethyl chloroformate and pyrridine or triethylamine in a solvent, such as 1,2-dimethoxyethane. After the addition, the mixture is heated briefly below reflux temperature, cooled and extracted with water and benzene. The organic extract is further washed with water and stripped of solvent to give the product.

A third method [(3) above] comprises the reaction of ethyl carbamate with a large excess of a phosphorus halide, as for example, phosphorus oxychloride, at about 60°C for approximately 3 hours. The excess phosphorus halide is stripped and the resulting product is reacted with two molar equivalents of the appropriate alcohol or phenol at up to 90°C to give the product.

The compounds are useful in a variety of lubricants. Those which may be improved by adding the phosphorus compound thereto are mineral and synthesized lubricating oils, as well as greases made therefrom. The mineral oils will be understood to embrace not only the paraffinic, but also the naphthenic and aromatic-containing members. By synthesized oils are meant synthesized hydrocarbons, polyalkylene oxide oils, polyacetals, polysilicones and the like, as well as synthetic ester oils. Of the latter type, there may be mentioned esters made from monohydric alcohols and polycarboxylic acids, such as 2-ethylhexyl azelate and the like, and those made from polyhydric alcohols and aliphatic monocarboxylic acids. Those of this group are especially important, and they include esters prepared from the polymethylols, as for example, the trimethylols, such as ethane, propane and butane derivatives thereof, 2,2-disubstituted propanediols and the pentaerythritols with aliphatic monocarboxylic acids containing from about 4 to about 9 carbon atoms. Mixtures of these acids may be used to prepare the esters. Examples of oils in this class are the esters prepared from a pentaerythritol and a mixture of $C_5$–$C_9$ acids. In making such esters, a generally acceptable product can be made from commercial pentaerythritol containing about 88% monopentaerythritol and 12% dipentaerythritol.

Having described the invention in general terms, the following are offered as specific embodiments thereof. It will be understood that the examples are merely for the purpose of the illustration, and there is no intention to limit the scope of the invention to the members shown.

The following Example specifically illustrates a method for preparing a compound useful in the practice of this invention.

of the test, the steel balls are examined for wear scar. The extent of scaring represents the effectiveness of the antiwear agent in the lubricant. The tests were carried out for 30 minutes each under a 60Kg load for the times, temperatures and at the speeds shown in Table 1.

TABLE 1

FOUR BALL WEAR TEST

| Example | | Conc., % by wt. | Temp. °F | Scar Diameter at | | | |
|---|---|---|---|---|---|---|---|
| | | | | 500RPM | 1000RPM | 1500RPM | 2000RPM |
| 1. | None (Lube only) | | 200 | 0.55 | 0.85 | 1.84 | 2.23 |
| | | | 390 | 1.0 | 1.31 | 2.08 | — |
| 2. | $(C_9H_{19}\text{--}\langle O \rangle\text{--} O)_2\overset{O}{\overset{\|}{P}}NHCOOC_2H_5$ | 1 | 200 | — | 0.58 | 0.58 | 0.56 |
| | | 1 | 390 | 0.55 | 0.60 | 0.59 | 0.65 |
| 3. | $(C_8H_{17}O)_2\overset{O}{\overset{\|}{P}}NHCOOC_2H_5$ | 1 | 200 | 0.56 | 0.56 | 1.61 | — |
| | | 1 | 390 | 0.48 | 0.55 | 0.59 | 0.58 |
| 4. | $(C_4H_9O)_2\overset{O}{\overset{\|}{P}}NHCOOC_2H_5$ | 1 | 200 | 0.70 | 0.90 | 0.75 | 0.63 |
| | | 1 | 390 | 0.65 | 0.55 | 0.52 | 0.65 |
| 5. | $(C_9H_{19}\text{--}\langle O \rangle\text{--} O)_2PNHCO_2C_2H_5$ | 1 | 200 | 0.50 | 0.50 | 0.60 | 0.65 |
| | | 1 | 390 | 0.50 | 0.60 | 0.85 | 1.2 |
| 6. | $(C_8H_{17}O)_2PNHCO_2Et$ | 1 | 200 | 0.40 | 0.60 | 0.70 | 0.60 |
| | | 1 | 390 | 0.50 | 0.50 | 0.60 | 0.80 |
| 7. | $(C_4H_9O)_2PNHCO_2Et$ | 1 | 200 | 0.60 | 0.70 | 0.70 | 0.70 |
| | | 1 | 390 | 0.50 | 0.60 | 0.65 | 0.75 |

EXAMPLE

Phosphorus oxylchloride, 612g (4 moles) was charged into a reaction flask equipped with a mechanical stirrer, thermometer, an addition funnel and a condenser to which was attached a drying tube. While stirring at 60°C, a solution of 180g (2 moles) of ethyl carbamate was added dropwise. After the addition, the reaction mixture was heated at 50°–60°C for an additional 2 hours. The excess phosphorus oxychloride was removed by distillation and nitrogen purge at 80°–90°C. The reaction mixture was then filtered to give a clear product.

The above product, 82g (0.4 moles) and 200 ml of 1,2-dimethoxyethane were charged into a reaction flask, and while stirring under a slow nitrogen purge, a solution of 176g (0.4 moles) of nonylphenol in 100ml of 1,2-dimethoxyethane was added dropwise at 50°–60°C. After the addition, the mixture was refluxed for about 3½ hours, while being purged by nitrogen to remove HCl. The mixture was then stripped under vacuum (2mm Hg) at 110°–115°C, to give a clear viscous liquid product.

In Table 1, Examples 2, 3 and 4 were prepared according to the description in the above Example, with appropriate changes in reactants. Examples 5, 6 and 7 were made following general procedure (1) discussed hereinabove.

EVALUATION OF ADDITIVES

Four Ball Wear Test

In this test, three one-half inch steel balls of 52100 steel are held in a ball cup. A fourth ball positioned on a rotatable axis is brought into contact with the three balls and is rotated against them. The force with which the rotatable ball is held against the three stationary balls may be varied according to the desired load. The test lubricant (the lubricant is an SAE 90 solvent refined Mid-Continent mineral oil) is added to the ball cup and acts as a lubricant for the rotation. At the end

I claim:
1. A lubricant composition comprising a major proportion of a lubricant and a minor amount sufficient to impart load carrying properties thereto of a diorganophosphorus compound of the formula:

wherein R is a $C_1$–$C_{25}$ hydrocarbyl and $m$ is zero or one.

2. The composition of claim 1 wherein the lubricant is a mineral lubricating oil.

3. The composition of claim 1 wherein the compound is

4. The composition of claim 1 wherein the compound is

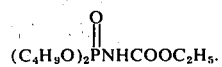

5. The composition of claim 1 wherein the compound is

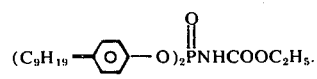

6. The composition of claim 1 wherein the compound is

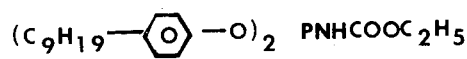

7. The composition of claim 1 wherein the compound is $(C_8H_{17}O)_2 PNHCOOC_2H_5$.

8. The composition of claim 1 wherein the compound is $(C_4H_9O)_2 PNHCOOC_2H_5$.

* * * * *